United States Patent [19]

D'Amelio et al.

[11] Patent Number: 4,659,195
[45] Date of Patent: Apr. 21, 1987

[54] ENGINE INSPECTION SYSTEM

[75] Inventors: Frank D. D'Amelio, Naugatuck; Michelle d. Maxfield, Stamford, both of Conn.; Dominick G. Esposito, Mamaroneck; Walter B. Kobyra, Bronx, both of N.Y.

[73] Assignee: American Hospital Supply Corporation, Evanston, Ill.

[21] Appl. No.: 824,846

[22] Filed: Jan. 31, 1986

[51] Int. Cl.$^4$ ............................................. G02B 7/00
[52] U.S. Cl. ........................................ 350/574; 128/4
[58] Field of Search ..................... 350/518, 563, 574; 128/4, 5, 6, 7, 8, 9–11

[56] References Cited

U.S. PATENT DOCUMENTS

| | | | |
|---|---|---|---|
| 2,348,752 | 5/1944 | Quayle | 174/29 |
| 2,975,785 | 3/1961 | Sheldon | 128/6 |
| 3,081,767 | 3/1963 | Hett | 128/6 |
| 3,506,331 | 4/1970 | Kompfner | 350/45 |
| 3,525,331 | 8/1970 | Mori | 350/96.25 |
| 3,557,780 | 1/1971 | Sato | 356/241 |
| 3,610,231 | 12/1971 | Takahashi et al. | 350/96.26 |
| 3,750,058 | 7/1973 | Bankert, Jr. et al. | 350/96.23 |
| 3,778,170 | 12/1973 | Howell et al. | 356/241 |
| 3,788,304 | 1/1974 | Takahashi | 350/96.25 |
| 4,078,864 | 3/1978 | Howell | 356/171 |
| 4,207,873 | 6/1980 | Kruy | 128/6 |
| 4,310,228 | 1/1982 | Terada | 128/6 |
| 4,349,014 | 9/1982 | Takamatsu | 128/6 |
| 4,530,568 | 7/1985 | Haduch et al. | 350/96.26 |

OTHER PUBLICATIONS

Olympus Corporation Technical Instruction of the Pratt & Whitney JT8D Combustion Chamber, pp. 1–8.

Primary Examiner—John K. Corbin
Assistant Examiner—Vincent J. Lemmo
Attorney, Agent, or Firm—Perman & Green

[57] ABSTRACT

An inspection system in which a fiber optic borescope has an elongated flexible body extending between a control head at a proximal end and an objective assembly at a distal end. The distal end is slidably inserted through a tubular elongated flexible guide member which has an operating head at a near end and a distal collar at a remote end capable of deflecting in four discrete directions. The objective assembly of the borescope is capable of deflecting in two discrete directions. A telescoping rigid support member connects the control head to the operating head and slidably receives the flexible body of the borescope. When the support member is retracted, the control head is proximate to the operating head and the objective assembly extends far beyond the distal collar. When the support member is extended, the control head is distant from the operating head and the objective assembly lies proximate to the distal collar. Cables for operating the distal collar extend between the near end and the remote end and each cable is operatively connected to the distal collar at one end and at the other end to an actuating element on the operating head for manual operation of the distal collar. A coil spring coaxial with the guide member extends between the operating head and the distal collar and firmly holds the operating cables against an inner surface of the guide member.

31 Claims, 26 Drawing Figures

ENGINE INSPECTION SYSTEM

BACKGROUND OF THE INVENTION

This invention relates to a flexible inspection system for use in both industrial and medical applications and, more particularly, to an elongatable, flexible, fiber optic inspection device slidably received in an external tubular guide member.

Elongated inspection devices, particularly such device incorporating flexible fiber optics, are often used to inspect sites which would not normally be visible to the human eye. The jet engine is one type of mechanical structure for which such inspection would be most useful, particularly to inspect the burner cans and the first stage, or high temperature stage, of the engine just behind the burner cans. These are among the components of the engine that are most subject to wear and deterioration. The arrangement of the jet engine's rotor and stator blades, particularly those in the high temperature stage of the engine, presents a most complex geometry which has not been amenable to inspection in the past other than by first disassembling the engine. There has been a need for some form of inspection device which can be placed near the rotor and stator blades, and other important sites within the engine, for the inspection thereof without the laborious task of disabling the engine. The use of this type of instrument would effect a substantial savings in the cost of maintenance of the engines. Savings would result from the man-hours saved by avoiding the disassembly and reassembly of the engine. Additional savings would result from the increase in service time of the engine since the downtime for maintenance would be substantially reduced.

A further appreciation of such tubular inspection devices can be more readily attained by considering those currently in use in the practice of medicine. For instance, a common form of such a device, known as an endoscope, is used for the inspection of the human colon while similarly structured device is used for inspection of the urethra. The endoscope is conventionally used in the diagnosis of tumors and other conditions in the lower gastrointestinal tract. The endoscopic examination involves the physician observing the intestinal wall through an eyepiece in the control head of the instrument. Generally, the endoscope, or colonoscope as it is termed in this procedure, is provided with a source of illumination at its objective end, the end which is placed adjacent the area to be examined, and a bundle of light-transmitting fibers through which an image of the examined area is transmitted back to the eyepiece. The endoscope can further incorporate a channel which provides a washing fluid for application to the site under examination as well as a surgical tip and other features. In other similar procedures the endoscope can be more specifically termed gastroscope and a bronchoscope.

A factor to be considered in the construction of the endoscope for its normal medical use is its flexibility and articulation which permits the objective tip to be directed along the channel of the colon. An endoscope can be made to traverse a considerable distance within the colon providing that any bends in the colon have a sufficiently large radius of curvature to enable the objective end of the endoscope to be readily articulated to follow the course of the colon. Care must be taken, however, to precisely guide the instrument so as not to puncture the colon wall, especially as the device is being inserted.

A problem arises in using presently available flexible devices for the internal inspection of complex articles of manufacture such as interior regions within jet engines. For example, certain compartments within the engine, such as the aforementioned regions within the burner cans and the turbine, are at present effectively inaccessible to viewing by an inspector. Such inaccessibility is the case even with the use of an inspection device such as an endoscope because the articulation of the inspection device requires some sort of guiding surface, such as the interior wall of the colon, to orient and support the inspection device. In contrast to the colon of the human body, a jet engine has an interior characterizied by relatively open spaces and few appropriate supporting surface readily available to guide the objective end of the inspection device. In addition, presently known endoscope designs, even when used for their originally intended purpose, are not easily able to negotiate all colon configurations without substantial risk of puncturing the colon wall.

As a result of recent catastrophic aircraft losses ostensibly caused by faulty internal jet engine structures and components, more frequent borescopic examinations have been mandated. This requires an inspection system which is easily used, which provides an optical image of highest clarity, and which can be readily inserted into the engine, then just as readily removed from the engine. A previously proposed solution to the problem calls for inspecting a number of different aspects of the jet engine and includes inspecting the burner cans arranged in a circular fashion. In order to inspect each aspect of each of the burner cans, the borescope must be inserted through one of two spark plug openings (typically in burner cans numbered seven and four, respectively, of a nine can construction) and then reach the remaining burner cans cans in the circle via the cross-over tubes connecting adjacent burner cans.

Currently available devices for performing such an inspection depend upon the combination of a guide tube which contains therein a viewing scope, the distal end of which can be extended from the end of the guide tube once the proper location is found. The purpose of this arrangement is to slip the guide tube in through the spark plug hole and up into the vicinity of the cross over tubes and then extend the viewing scope out of the distal end of the guide tube and into the cross over tube so that the guide tube can be fed into the next burner. Some known mechanisms for extending the viewing scope from the distal end of the guide tube include a scissors type of arrangement whereby the viewing scope is pushed farther into the guide tube from the proximal end thereof.

There are two major problems with the known devices incorporating the scissors arrangement for advancing the viewing scope into the guide tube. The first is that as the viewing scope holder is brought towards the proximal end of the guide tube to push the viewing scope therein, the viewing scope kinks up or arcs and this causes material fatigue of the viewing scope which tends to unravel the viewing scope and have it break apart. The second problem is that an operator of the known devices must use one hand to push the viewing scope holder towards the guide tube base and the other hand to feed the viewing scope tube into the entrance hole of the guide tube base. This is an extremely awkward maneuver and it would be best carried out if the operator had a third hand which would put a varying force on the kink created to make the feeding easier.

Additional problems with the known devices are that the guide tube can only articulate in two directions, i.e. in one plane, which makes it very awkward and time consuming to get the distal end thereof in the proper location for feeding the viewing scope through the crossover tubes. This is generally done by lining up in the plane by which articulation of the distal end thereof is possible and then jumping or jogging the cable around to exactly line it up so that the viewing scope can be located correctly. Finally, the known scopes cannot easily accomplish inspections of the louvered section of the burner can or the first stage stationary vanes and first rotor as they cannot be easily located in the center of the burner can for ease of such inspection.

SUMMARY OF THE INVENTION

The foregoing problems are overcome and other advantages are provided by an inspection device which is constructed according to the invention in a generally elongated format within a flexible outer sleeve or tubular guide member which is readily articulated in four directions. The inspection device includes an optical system for the transmission of illuminating light and the viewing of reflected light.

Specifically disclosed are an inspection system in which a fiber optic borescope has an elongated flexible body extending between a control head at a proximal end and a objective assembly at a distal end. The distal end is slidably inserted through a tubular elongated flexible guide member which has an operating head at a near end and a distal collar at a remote end capable of deflecting in four discrete directions. The objective assembly of the borescope is capable of deflecting in two discrete directions. In the embodiment, a telescoping rigid support member connects the control head to the operating head and slidably receives the flexible body of the borescope. When the support member is retracted, the control head is proximate to the operating head and the objective assembly extends far beyond the distal collar. When the support member is extended, the control head is distant from the operating head and the objective assembly lies proximate to the distal collar. Cables for operating the distal collar extend between the near end and the remote end and each cable is operatively connected to the distal collar at one end and at the other end to an actuating element on the operating head for manual operation of the distal collar. A coil spring coaxial with the guide member extends between the operating head and the distal collar and firmly holds the operating cables against an inner surface of the guide member.

It will be appreciated that the amount of maneuvering required by the inspection device is extreme throughout the engine in order to accomplish an adequate inspection. The agility of the device is therefore extremely important.

The device of the invention provides for a four-way (two-plane) articulation of the flexible guide tube whereas known devices provide for only a two-way (one-plane) articulation of the guide tube. As with the prior art, the present invention also provides for a two-way (one-plane) articulation of the viewing scope or borescope. Additionally, the invention replaces the very awkward and hard to use scissors mechanism, previously mentioned, with a more easily useable, mechanism between the guide tube and the viewing scope or borescope. The mechanism can be a substantially rigid support member intermediate the control head and operating head with means for enabling improvement of the support member in a linear or straight fashion in and out of the flexible guide tube. Such mechanisms can be the telescoping type.

The telescoping mechanism is constructed so as to collapse as the distal end of the viewing scope is extended and it is extended to its full length when the distal end of the viewing scope is fully retracted. One end of the telescoping mechanism is attached to the flexible guide tube housing while the opposite end is attached to the viewing scope housing. To operate or extend the working or distal end of the viewing scope out of the flexible tube, the operator need only slide or push the viewing scope housing towards the flexible guide housing to collapse the telescoping mechanism and thus push the distal end of the viewing scope into its extended position. To retract the distal end of the viewing scope, the operator need only slide the viewing scope housing away from the flexible guide tube housing to expand the telescoping mechanism thereby retracting the distal end of the viewing scope towards the distal end of the flexible guide tube housing. As can be appreciated, this is a very easy operation, especially when compared to prior art scissor mechanisms, and there is no need for guiding the viewing scope from a kinked, curved, or out-of-line position into the flexible tube, which is much more fatiguing.

Other and further features, objects advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of this invention, illustrate some of the embodiments of the invention and, together with the description, serve to explain the principles of the invention in general terms.

DETAILED DESCRIPTION OF THE DRAWINGS

DETAILED DESCRIPTION OF THE PREFERRED EMBODIMENT

Figure 1:
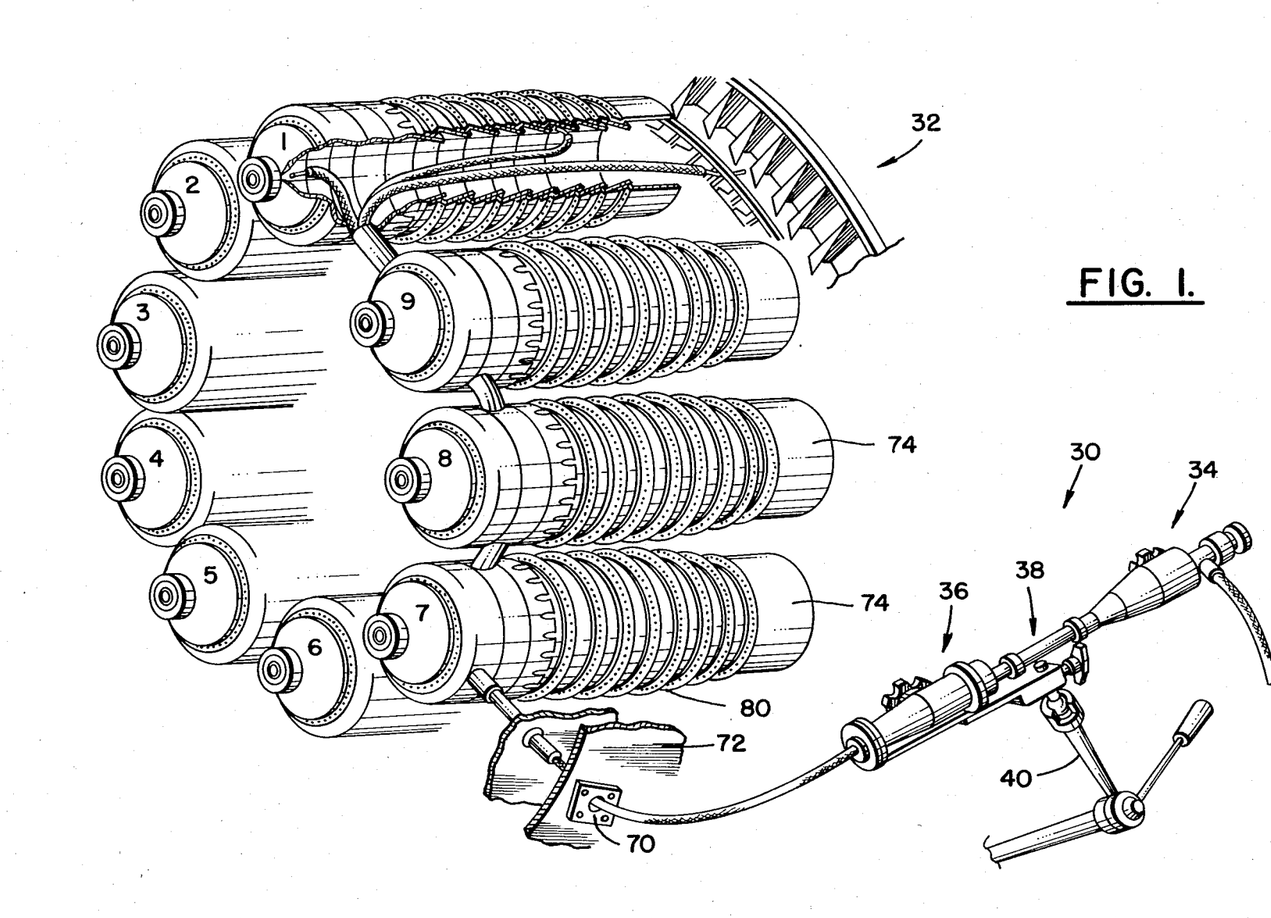
FIG. 1 is detail perspective view of a portion of a jet engine being inspected by the optical inspection system of the invention, certain parts being cut away and in section.
Figure 2:
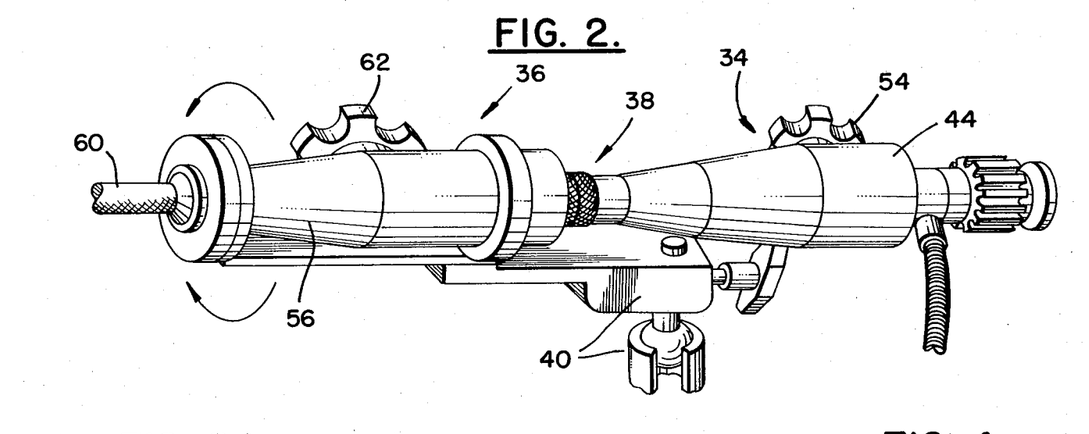
FIG. 2 is a detail perspective view illustrating the control head of a borescope and the operating head of a guide member in mutually proximate positions.
Figure 3:
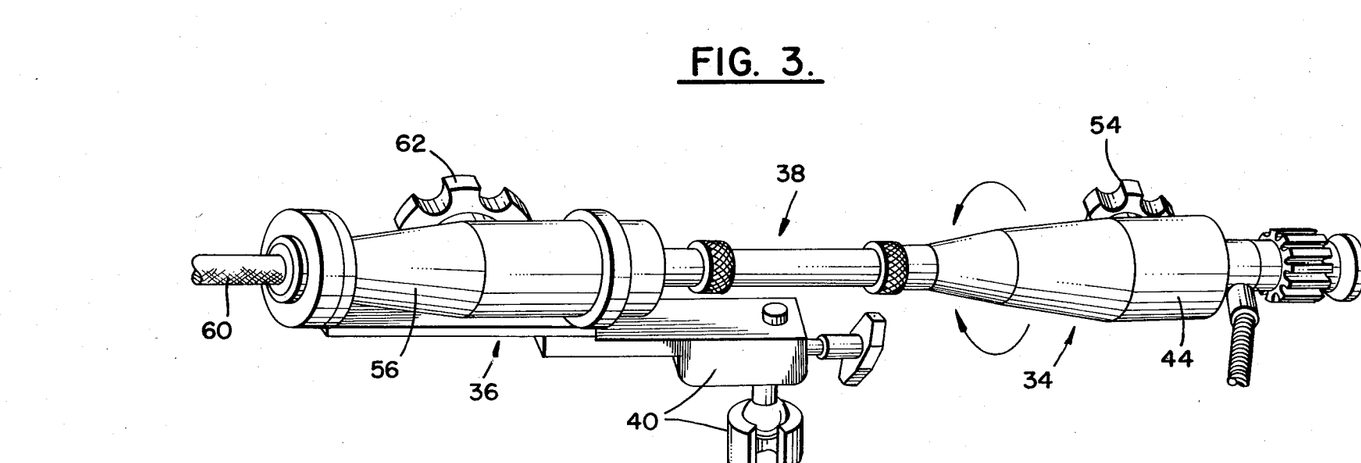
FIG. 3 is a detail perspective view, similar to FIG. 2, illustrating the control head and the operating head positioned in spaced apart relationship.

Turn now to the drawings and initially to FIGS. 1-3 which illustrates an optical inspection system 30 embodying the invention and depicting its use in the inspection of portions of the interior of a jet engine 32. The inspection system 30 includes a borescope 34, a guide member 36, and a telescoping support member 38 connecting the borescope to the guide member. A suitable clamp 40 is utilized for mounting the inspection system 30 in an appropriate fashion next to the portions of the engine to be inspected.

Figure 2A:
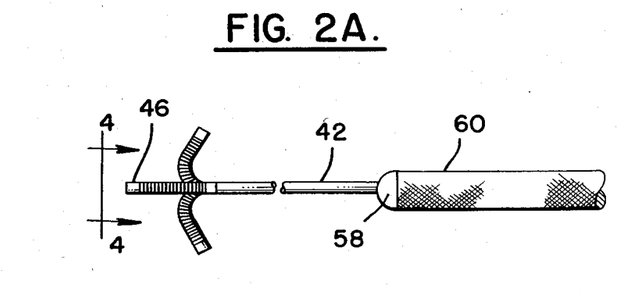
FIG. 2A is a detail perspective view of a distal end of the inspection system in extended and articulated positions resulting from the position of the components illustrated in FIG. 2.
Figure 3A:
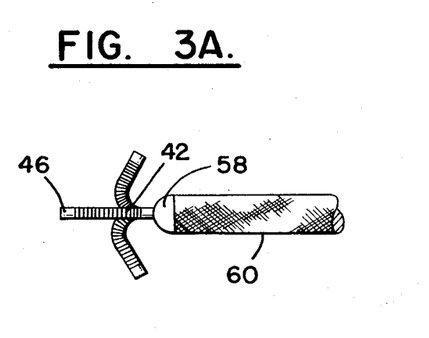
FIGS. 3A is a detail perspective view (similar to FIG. 2A) of a distal end of the inspection system in retracted and articulated positions resulting from the position of the components illustrated in FIG. 3.
Figure 4:
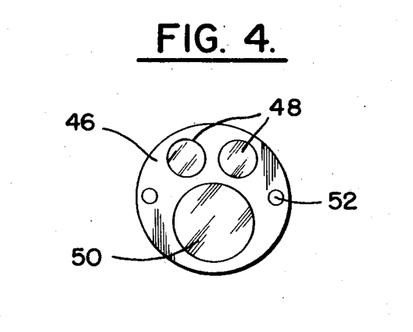
FIG. 4 is an end elevation view as seen from line 4—4 in FIG. 2A.
Figure 5:
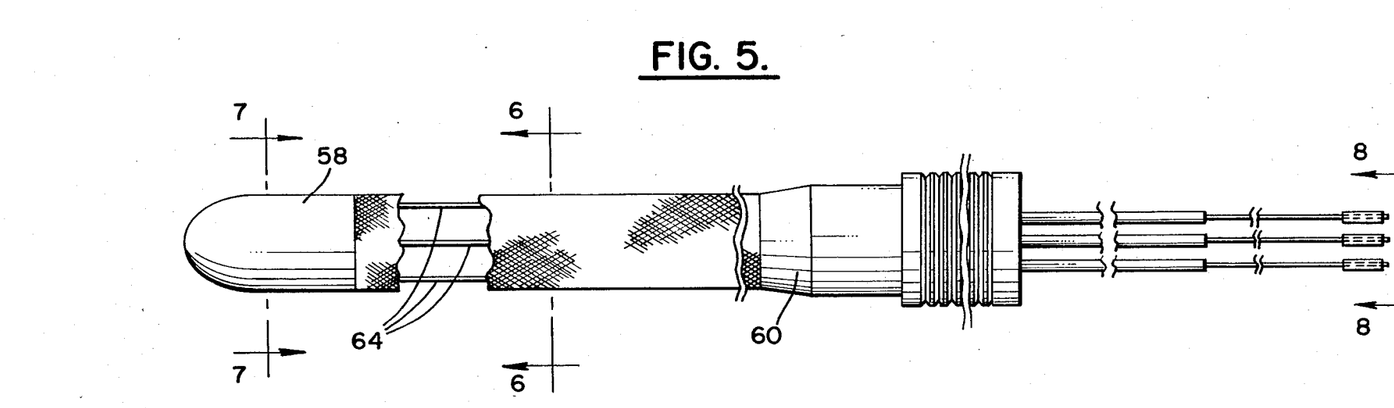
FIG. 5 is a side elevation view of the guide member of the invention, certain parts being cut away and in section and certain other parts being shortened for ease of illustration.
Figure 6:
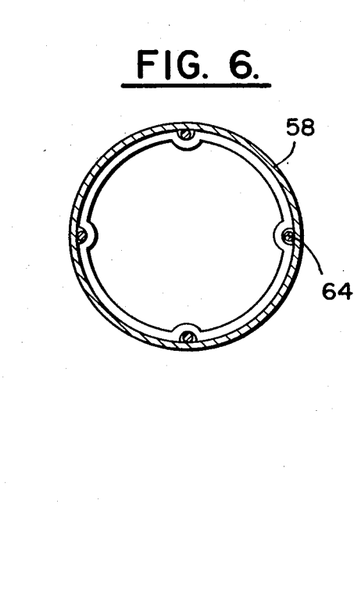
FIG. 6 is a cross section view taken generally along line 6—6 in FIG. 5.
Figure 7:
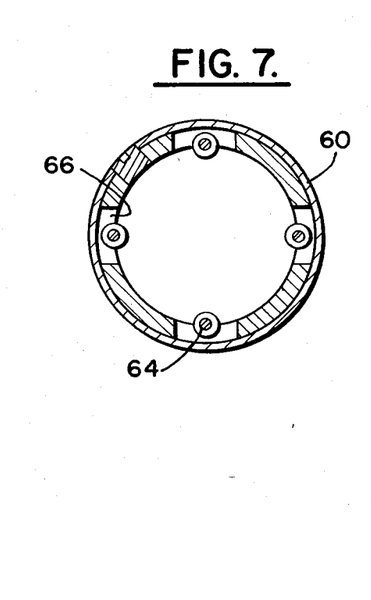
FIG. 7 is an end elevation view taken generally along line 7—7 in FIG. 5.
Figure 8:
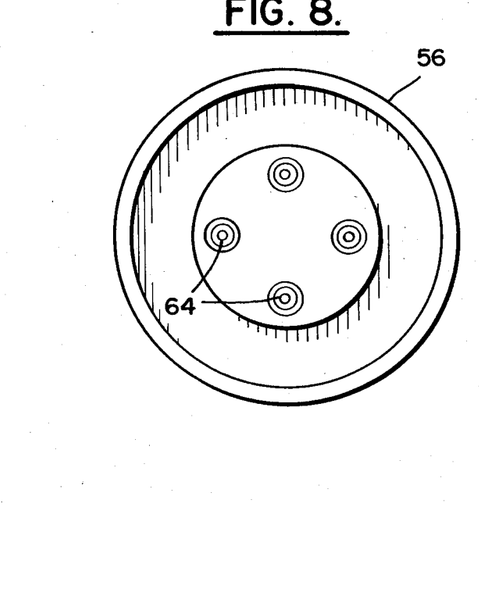
FIG. 8 is an end elevation view as seen from line 8—8 in FIG. 5.

Turning now to FIGS. 2 and 2A, and to FIGS. 3 and 3A, the borescope 34 has a generally elongated flexible body 42 (FIGS. 2A) which extends between a control head 44 at a proximal end thereof (FIGS. 2 and 3) and an objective assembly 46 at a distal end thereof. The borescope 34 may be of a known design, one example being Model No.: BFM227ODDX manufactured by American ACMI Division of American Hospital Supply Corporation. In a typical arrangement, as seen in FIG. 4, the objective assembly 46 represents the terminal end of the borescope 34 which incorporates three optical components, twin fiber optics bundles 48 providing illumination to the area being examined and one larger imaging components 50 is used for remote viewing. Various types of optical components may be used for the imaging component, such as a fiber optical system, electronic imaging system, or rigid optical system as described in the prior art, for example, U.S. Pat. Nos. 4,207,873 to Kury; 4,349,014 to Takamatsu and 4,310,228 to Terada. In addition, cable ends 52 are depicted, operable by a control knob 54 on the control head 44 (FIGS. 2 and 3). The control knob 54 operated in a known fashion to enable the objective assembly 46 at the distal end of the borescope to be articulated in two directions lying in one plane as depicted by dotted lines in FIGS. 2A and 3A. The particular control mechanism which enables articulation of the distal end of the flexible body 42, and therefore the objective assembly 46, may be generally as shown and described in commonly assigned U.S. Pat. No. 4,207,873 issued June 17, 1980 to Kruy et al.

Figure 9:
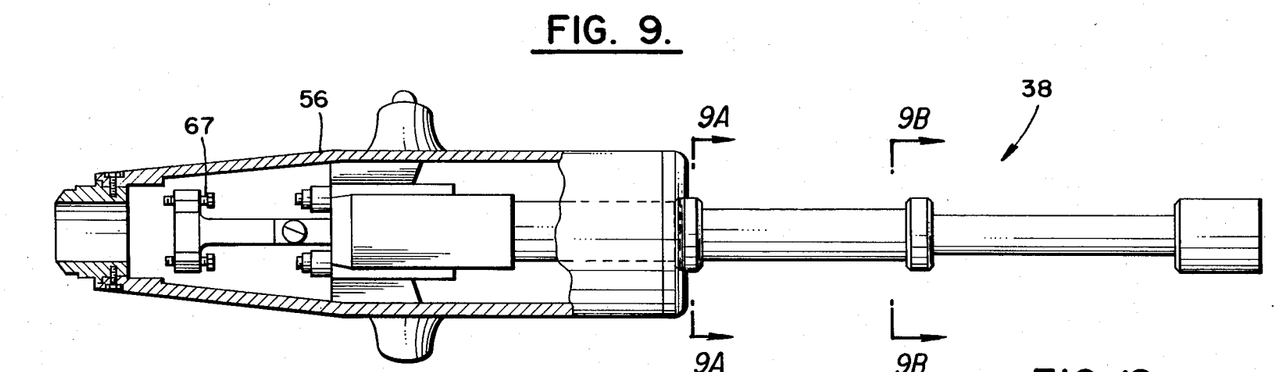
FIG. 9 is a side elevation view of a telescopic mechanism in its extended position as part of the control head of the flexible guide member, certain parts being cut away and in section.
Figure 10:
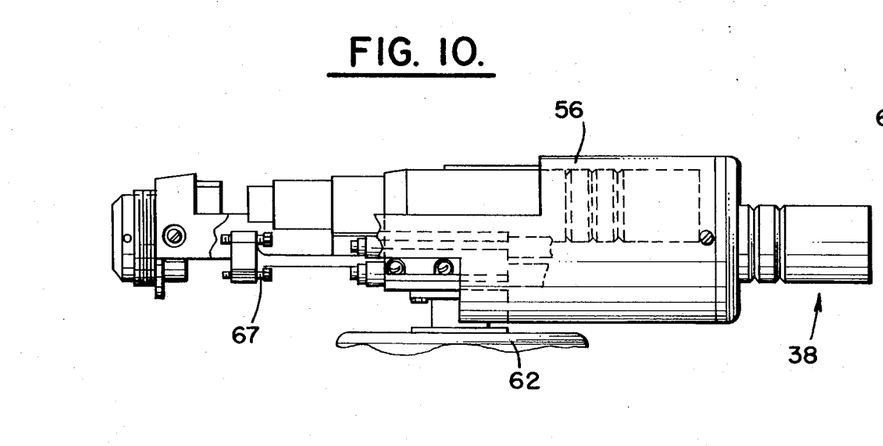
FIG. 10 is a top plan view illustrating a portion of the construction illustrated in FIG. 9.

The guide member 36 includes an operating head 56 at a near end (FIGS. 2 and 3), a distal collar 58 at a remote end (FIGS. 2A and 3A), and a tubular elongated flexible member 60 fixed at its near end to the operating head 56, the distal collar 58 being attached to its remote end. An operative mechanism in the form of an actuating knobs 62 and 63 is mounted on the operating head 56 and serves to deflect the distal collar in at least four discrete directions lying in two transverse planes. As best seen in FIGS. 5-8, a plurality of operating cables 64 extend along an inner surface 66 of the tubular member 60. The operating cables 64 are suitably joined at their remote ends to the distal collar 58 (see FIG. 7) and at their near ends to suitable retainer members 67 of the operating head 56 (see FIGS. 9-10). The operating mechanism for the guide member 36 may be generally as shown and described in commonly assigned U.S. Pat. No. 4,530,568 issued July 23, 1985 to Haduch et al, but with the fiber optical portions removed from the flexible member 60. With the cables 64 placed at spaced circumferential locations around the inner surface 66, the distal collar 58 can be moved in as many directions as there are cables. Since there are four cables at equally spaced circumferential locations in the illustrated embodiment, that construction provides movement in four different directions lying in two different intersecting planes.

Figure 9A:
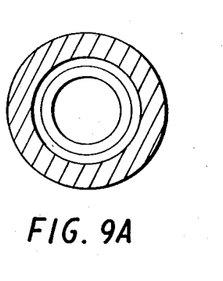
FIGS. 9A and 9B are enlarged sectional views taken through FIGS. 9A & 9B respectively, of FIG. 9 showing the telescopic section mechanism.
Figure 9B:
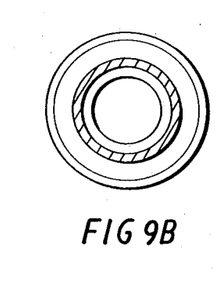
Figure 11:
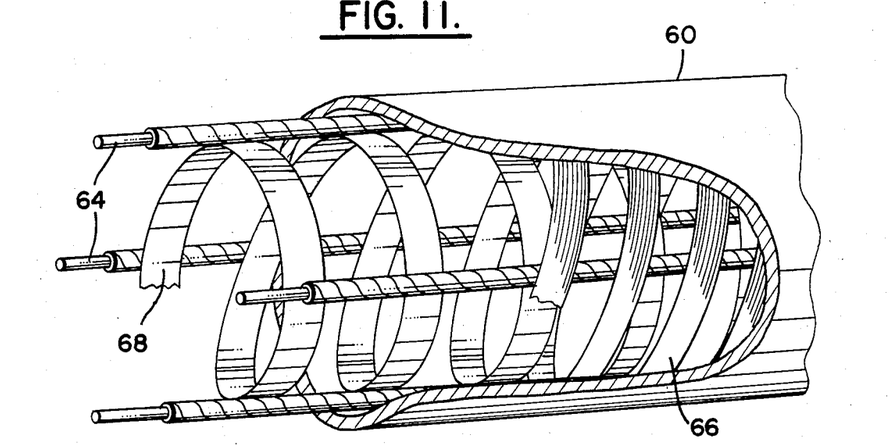
FIG. 11 is a perspective detail view of the guide member alone with certain parts being cut away and in section in order to illustrate the retention member for maintaining the position of the operating cables.
Figure 12:
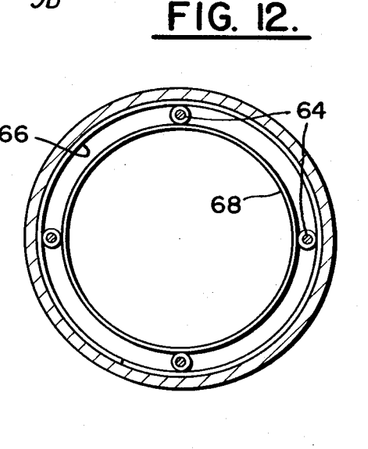
FIG. 12 is an elevational cross section view of the construction illustrated in FIG. 11.

Return now to FIGS. 2A and 3A which depict, respectively, the extended and retracted positions of the objective assembly 46 relative to the distal collar 58. Extension and retraction of the telescoping support member 38, as shown in FIGS. 9A and 9B is effected by rotating knurled nuts 38A AND 38B to grasp and release the internal tubular members in the conventional fashion. Such relative movement between the borescope 34 and the support member 38 is for a number of reasons. These reasons include easier insertion of the optical system 30 into the engine to be examined, and retraction therefrom, greater ability to view those structures being inspected, and protection of the objective assembly 46 as the borescope 34 is being advanced into or withdrawn from the interior of the jet engine. In any event, when the support member 38 is in a retracted condition at which the control head 44 is positioned proximate to the operating head 56, the flexible body 42 of the borescope 34 is in an extended position such that the objective assembly 46 lies distant from and beyond the distal collar 58 as seen in FIGS. 2A. Conversely, when the support member 38 is in the extended condition illustrated in FIG. 3 such that the control head 44 is positioned distant from the operating head 56, the flexible body 42 is retracted such that the objective assembly 46 lies proximate to the distal collar 58. However, it will be appreciated that even in the retracted position of the flexible body 42, the objective assembly 46 can still be manipulated to the dotted line positions indicated in FIG. 3A. In its retracted position, the objective assembly 46 may typically extend approximately 1.4 to 2.0 inches beyond the distal collar 58 and in the extended position, approximately 6 to 8 inches or longer beyond the distal collar 58. Another aspect of the invention is illustrated in FIGS. 11 and 12. Even though the operating cables 64 which articulate the ends of the flexible member 60 are anchored at their distal ends to the distal collar 58 and at their proximal ends to suitable retainer members 67 (see FIGS. 9 and 10), there is a fairly long run of cables between the two ends which tend to become twisted and interfere with the movement of the various parts of the mechanism. A solution to this problem is illustrated in FIGS. 11 and 12 and comprises a spiral retention member such as a channel-like tube coil spring 68 received within the tubular member 60 and outwardly biased in order to firmly hold the operating cables against the inner surface 66. The retention spring 68 is preferably fashioned from flat stock so as to occupy minimal space when viewing the tubular member 60 from an end. The retention spring thus serves to retain the operating cables 64 and their surrounding sheaths in their proper respective positions even though the borescope 34 is twisted relative to the tubular member 60.

Specifically, the retention spring 68 prevents the operating cables 64 from spiraling with the borescope 34 as the latter is spun inside the tubular member 60. In the absence of the retention spring 68, the operating cables 64 would tend to spin with the borescope 34 which would not only cause interference between the borescope and the tubular member 60, but also would cause unreasonable and unnecessary wear on the parts. Furthermore, the flexibility of the retention spring 68 assures that it will not adversely affect the flexiblity of the tubular member 60. The structure which has just been described possesses a number of structural differences from the devices of the prior art. These differences include the capability of the guide member 36 having four-way, that is, two-plane articulation. Additionally, by reason of the support member 38, the flexible body 42 of the borescope 34 is held substantially straight between its own control head 44 and the distal end of the operating head 56 as the flexible body 42 is being advanced and withdrawn relative to the tubular member 60.

Also, the prior art is devoid of any showing or suggestion of any construction remotely similar to the support member 38 with its telescoping construction. Another significant structural difference and improvement over the prior art is provided by the spiral retention spring 68 which assures unhampered fail safe operation of the inspection system.

To operate the invention, with initial reference to FIG. 1, a friction plate 70 is mounted to igniter plug boss 72 following removal of an igniter plug (not shown). This is preferably accomplished at the number 4 or the number 7 position of the plurality of burner cans 74 of the jet engine 32. FIG. 1, by way of example, is illustrative of a nine burner can arrangement characteristic of the Pratt and Whitney JT8D jet engine. The support arm clamp 40 with the optical inspection system 30 securely mounted thereon is suitably secured to a rigid component of the engine 32. The distal end of the guide member 36 is then suitably positioned adjacent the friction plate 70 to permit insertion of the objective assembly 46 and distal collar 58 into the burner can 74 numbered 7 in FIG. 1.

Figure 13:
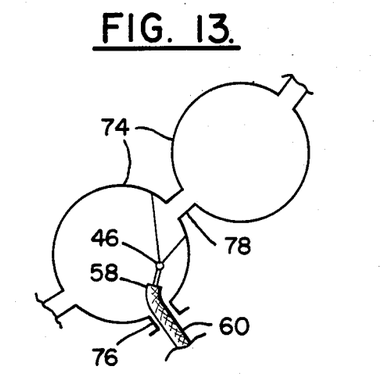
FIGS. 13 thru 19 are diagrammatic illustrations generally depicting the operation of the invention.
Figure 14:
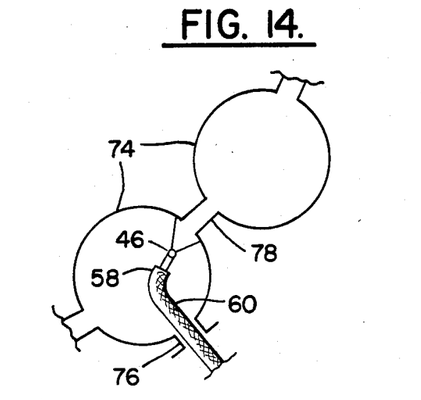
Figure 15:
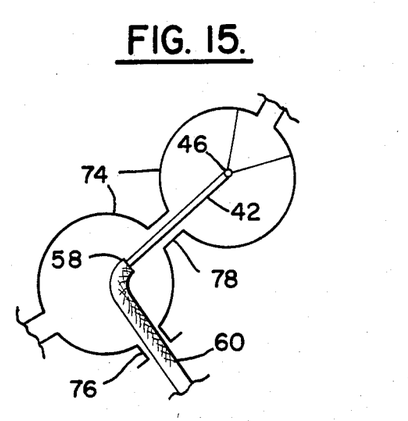
Figure 16:
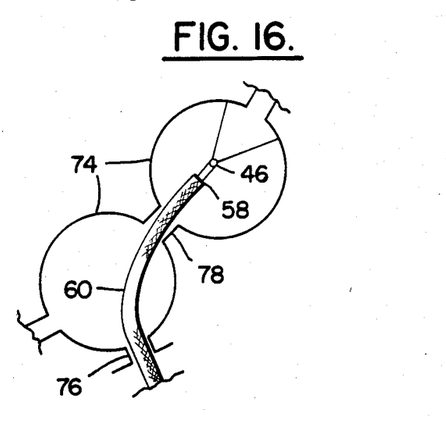

With the control knob 54 and actuating knob 62 in their neutral positions, the distal ends of the borescope 34 and of the guide member 36 are together inserted into the burner can. In a typical maneuver, as illustrated in FIG. 13, while the objective assembly 46 is viewing the liner of the burner can 74 opposite the igniter port 76, the distal collar 58 is articulated by means of the actuating knobs 62 and 63 to enable the objective assembly 46 to locate a crossover tube 78 between the adjacent burner cans 74. With continued manipulation by the operator of the inspection system 30, the distal collar 58 is moved closer to the crossover tube 78 as illustrated in FIG. 14 while keeping the tube 78 in the center of view of the objective assembly 46. When the FIG. 14 position is reached, the objective assembly 46 is advanced by moving the control head 44 to a position proximate to the operating head 56. In this manner, the flexible body 42 is inserted through the crossover tube 78 into the adjacent burner can 74, as seen in FIG. 15. Then, with the actuating knob 62 placed in its neutral position, the operating head is moved by the operator away from the control head 44, extending the support member 38. In this manner, the tubular member follows along the flexible body 42 until the distal collar 58 is once again closest to the objective assembly 46. This step is indicated in FIG. 16. As the tubular member 60 advances along the flexible body 42, the objective assembly 46 maintains a constant view of the liner opposite the tube 78 this procedure is repeated until the borescope 34 and guide member 36 have passed through the desired number of burner cans.

Figure 17:
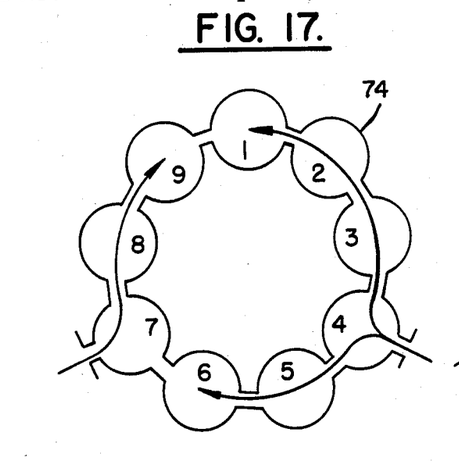
Figure 18:
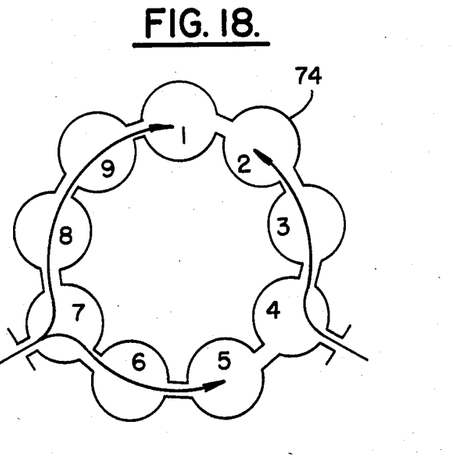
Figure 19:
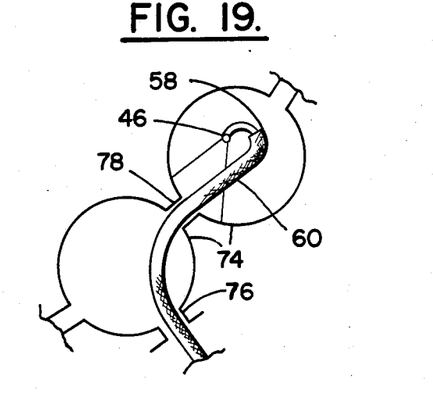

Alternative procedures are illustrated diagrammatically in FIGS. 17 and 18. As illustrated, the optical inspection system 30 can enter up to five burner cans with one insertion, but only four cans can be completely inspected. During this entire procedure, areas of interest within the burner cans can be inspected by articulating the objective assembly 46 and the distal collar 58, feeding the system 30 to an extreme end of a burner can, then extending the objective assembly 46. The inspection itself is performed as the system 30 is withdrawn from each burner can. To inspect an area around a crossover tube through which the objective assembly 46 and distal collar 58 are inserted is generally illustrated in FIG. 19. For this view, the objective assembly 46 must articulate in the same plane as the guide member 36.

Figure 20:
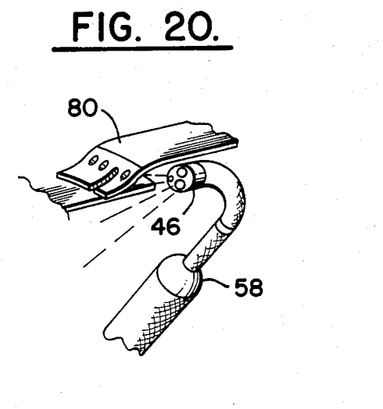
FIGS. 20 through 22 are detail perspective views illustrating various inspection operations performed by the invention.

There are numerous advantages inherent in the present invention over the known devices. In the first place, the four-way articulation of the steerable flexible guide member 36 allows a quicker, more precise positioning of its distal end before the objective assembly 46 is extended. This is important because of the different positional locations between the igniter port 76 and the crossover tubes 78 and other elements to be inspected by the device. Additionally, by reason of the disclosed construction, and specifically the support member 38, there is minimal wear on the flexible body 42 of the borescope 34. Also, as illustrated in FIG. 20, which is illustrative of one dotted line positioning of the inspection system 30 within a burner can as depicted in FIG. 1, viewing of a louvered area 80 of the burner cans is more easily accomplished by the invention. This is done by placing the distal end of a flexible guide member 36 in the center of the burner can 74 as illustrated by dotted lines in FIG. 1. The invention, by virtue of its four-way articulation, permits the distal collar 58 to be easily placed in the center of the burner can and then to spin or rotate the objective assembly 46, which is positioned near the louvered area 80, in a 360 degree arc so as to inspect each one of the louvers. This easily performed operation contrasts with the prior art constructions which are restricted by a two-way articulation at the end of their equivalent of the tubular member 60. Such prior art devices cannot be positioned very easily in the center of a burner can but must be located in several positions in order to inspect all of the louvers around the outside of the burner can.

Figure 21:
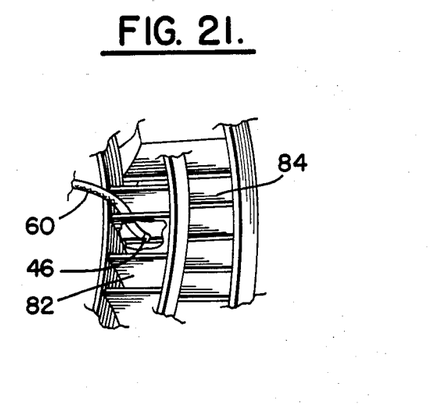

It is also noteworthy that the first stage of the jet engine 32 can be much more easily viewed by the invention. This is depicted in FIG. 21 which illustrates the distal collar 58 being precisely located within the burner can next to the fixed guide vanes 82 of the first stage of the jet engine 32. In this manner, the objective assembly 46 can be fed through the vanes in a precise manner and displaced accurately adjacent the first stage rotor 84. The rotor can then be turned by hand for complete inspection by the system 30. While the prior art can theoretically accomplish this end result, the fact is that in order to inspect the rotor 84 and the fixed guide vanes 82, the objective assembly 46 must repositioned several times because of the awkwardness in positioning it in the first place. This awkwardness results from the limited two way articulation system previously employed. Thus, the known inspection systems must work around the area to be inspected with several positions for the end of the guide tube. In contrast, the invention merely requires that the distal collar 58 be set near the center of the burner can so that when the objective assembly 46 of the borescope 34 is fully extended, it will be in the precise position to get into the rotor area.

Figure 22:
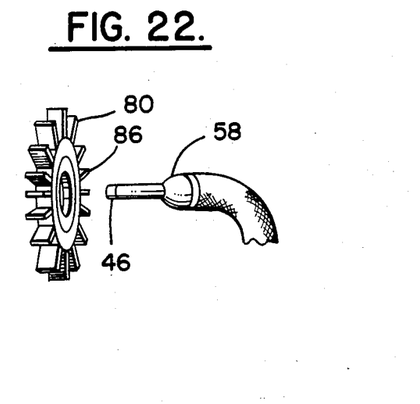

FIG. 22 illustrates another common position required of the inspection system 30 within the burner can 74. Specifically, the distal collar 58 is manipulated so as to be generally aligned with an interface of a fuel nozzle 86 and fuel swirler 88. This positioning is desirable because burner may shift can be evidenced by misalignment of, or excessive recessing of, the fuel nozzle 86 and fuel swirler 88 interface. This positioning of the distal collar can, once again, be readily achieved by reason of the four way articulation provided by the guide member 36.

The invention thus provides with a one hand operation, for easy extension and retraction of the distal end of the borescope 34. The prior art devices failed more quickly and more often than the invention by reason of the necessity to push and guide the equivalent of the flexible body 42 into the tubular member 60 at the operating head 56. In constrast, by reason of the invention, a push and feed arrangement is provided through the support member 38 with consequent relief of stress and wear on the flexible body 42 of the borescope 34. Also, it should be noted that when the control head 44 is moved relative to the operating head 56 and spun or rotated in a concentric manner with the tubular member 60, the proximal end thereof is relatively linear and rigid.

Another element of the construction of the present invention which adds considerably to the reliability of the invention is the provision of the retention spring 68 which eliminates potential problems of the operating cables 64 twisting with the flexible body 42 as the latter is spun or rotated inside the tubular member 60.

Another impressive benefit of the pressent invention resides in the significant savings in time which it achieves for the jet engine inspection process. This is particularly important in feeding the inspection system 30 into the burner cans and through the crossover tubes to get the farthest burner can. This is of substantial importance by reason of the large number of engines to be inspected.

It is to be understood that the above described embodiment of the invention is illustrative only, and that modifications thereof may occur to those skilled in the art. Accordingly, this invention is not to be regarded as limited to the embodiment disclosed herein. Any type of elongated substantially rigid support member intermediate the control head and operating head can be used including alternative designs such as those that enable the head and member to move in a straight or linear fashion in and out of the flexible guide member. Indeed, the invention is applicable to a variety of other industrial uses apart from inspection of the interior of a jet engine and can have medical applications as well. Also, while the optical system has been described therein as utilizing fiber optic bundles, the invention is intended to encompass other types of optical systems including, but not necessarily limited to, rigid optical systems and electronic imaging systems. Thus, the scope of the invention is defined by the appended claims rather than by the foregoing description, and all the changes which come within the meaning and range of equivalency of the claims are intended to be embraced herein.

We claim:

1. In an inspection instrument having a generally elongated flexible body extending between a control head at a proximal end thereof and an objective assembly at a distal end thereof for viewing subject matter to be inspected, the improved comprising:
    a tubular elongated flexible guide member adapted to slidably receive said body therethrough including:
    an operating head at a near end of said guide member; and
    a distal collar at a remote end of said guide member capable of deflection in at least four discrete directions;
    whereby said guide member is effective to similarly move said objective assembly when said distal end is generally coextensive with said remote end.
2. An instrument as set forth in claim 1 including:
    operative means for deflecting said distal collar in at least four discrete directions.
3. An instrument as set forth in claim 2 wherein said operative means includes:
    a plurality of actuating elements movably mounted on said operating head; and
    a plurality of operating cables extending between said near end and said remote end, each of said operating cables being operatively connected to said distal collar and to one of said actuating elements, respectively;
    whereby movement of each of said actuating elements is effective to deflect said distal collar in one of said directions.
4. An instrument as set forth in claim 3
    wherein said guide member has an interior surface;
    wherein said operating cables extend alongside said interior surface; and
    including:
    retention means within said guide member engageable with said operating cables and biasing said operating cables against said interior surface.
5. An instrument as set forth in claim 4
    wherein said retention means is a coil spring coaxial with said guide member
    and extending between said operating head and said distal collar.
6. An instrument as set forth in claim 1 including:
    a tubular elongated rigid support member intermediate said control head and said operating head and attached at its ends, respectively, to said control head and said operating head, said support member adapted to slidably receive said body therein.

7. An instrument as set forth in claim 6 wherein said control head, said operating head, and said support member are all axially aligned.

8. An instrument as set forth in claim 4 wherein said support member includes:
a plurality of coaxial telescoping sections movable between a retracted condition at which said control head is positioned proximate to said operating head and an extended condition at which said control head is positioned distant from said operating head.

9. An instrument as set forth in claim 8
wherein said objective assembly lies proximate to said distal collar when said support member assumes the extended condition and lies distant from and beyond said distal collar when said support member assumes the retracted condition.

10. An instrument as set forth in claim 1
wherein said body includes an optical system for transmitting to said control head an image of the subject matter to be inspected.

11. An instrument as set forth in claim 10
wherein said optical system is one of a fiber optical system, a rigid optical system, and an electronic imaging system.

12. An instrument as set forth in claim 1
wherein said objective assembly includes:
a terminal bushing at an extremity of said distal end; and
a bending section adjacent said terminal bushing enabling deflection of said terminal bushing in at least two discrete directions.

13. An instrument as set forth in claim 12
wherein said instrument includes:
control means for deflecting said terminal bushing in at least two discrete directions 14. An instrument as set forth in claim 13
wherein said control means includes:
a plurality of actuating elements movably mounted on said control head; and
a plurality of control cables extending between said proximal end and said distal end, each of said control cables being operatively connected to said terminal bushing and to one of said actuating elements, respectively;
whereby movement of each of said actuating elements is effective to deflect said terminal bushing in one of said directions.

15. In an elongated flexible borescope including an operating head at its proximal end and a deflectable section at its distal end, a tubular member having an interior surface extending between said operating head and said deflectable section, and deflection control means including operating cables extending within said tubular member alongside said interior surface between said proximal end and said distal end, the improvement comprising:
retention means within said tubular member engageable with said operating cables and biasing said operating cables against said interior surface.

16. A borescope as set forth in claim 15
wherein said retention means is a coil spring coaxial with said tubular member and extending between said operating head and said deflectable section.

17. In an inspection instrument having a generally elongated flexible body extending between a control head at a proximal end thereof and an objective assembly at a distal end thereof for viewing subject matter to be inspected, the improvement comprising:
a tubular elongated flexible guide member having an interior surface and adapted to slidably receive said flexible body therethrough including:
an operating head at a near end of said guide member;
a distal collar at a remote end of said guide member capable of deflection in at least four discrete directions; and
operative means for deflecting said distal collar including:
a plurality of actuating elements movably mounted on said operating head; and
a plurality of operating cables extending between said near end and said remote end along said said interior surface, each of said operating cables being operatively connected to said distal collar and to one of said actuating elements, respectively, such that movement of each of said actuating elements is effective to deflect said distal collar in one of said directions;
said inspection instrument including:
a tubular elongated rigid support member intermediate said control head and said operating head and attached at its ends, respectively, to said control head and said operating head, said support member adapted to slidably receive said body therein and including:
a plurality of coaxial telescoping sections movable between a retracted condition at which said control head is positioned proximate to said operating head and an extended condition at which said control head is positioned distant from said operating head, said objective assembly lying proximate to said distal collar when said support member assumes the extended condition and lying distant from and beyond said distal collar when said support member assumes the retracted condition; and
said inspection instrument including:
retention means within said guide member engageable with said operating cables and biasing said operating cables against said interior surface.

18. An instrument as set forth in claim 17 wherein said retention means is a coil spring coaxial with said guide member and extending between said operating head and said distal collar.

19. An instrument as set forth in claim 17 wherein said control head, said operating head, and said support member are all axially aligned.

20. An instrument as set forth in claim 17
wherein said body includes an optical system for transmitting to said control head an image of the subject matter to be inspected.

21. An instrument as set forth in claim 20
wherein said optical system is one of a fiber optical system, a rigid optical system, and an electronic imaging system.

22. An instrument as set forth in claim 17
wherein said objective assembly includes a terminal bushing at an extremity of said distal end; and
a bending section adjacent said terminal bushing enabling deflection of said terminal bushing in at least two discrete directions.

23. An instrument as set forth in claim 22
wherein said instrument includes:
control means for deflecting said terminal bushing in at least two discrete directions.

24. In an inspection instrument having a generally elongated flexible body extending between a control head at a proximal end thereof and an objective assembly at a distal end thereof for viewing subject matter to be inspected, the improvement comprising:
   a tubular elongated flexible guide member adapted to slidably receive said body therethrough including:
   an operating head at a near end of said guide member;
   a distal collar at a remote end of said guide member capable of deflection in at least two discrete direction whereby said guide member is effective to similarly move said objective assembly when said distal end is generally coextensive with said remote end; and
   an elongated substantially rigid support member intermediate said control head and said operating head and attached at its ends, respectively to said control head and said operating head, said support member adapted to slidably receive said body therein;
   wherein said support member includes:
   means for moving between a retracted condition at which said control head is positioned proximate to said operating head and an extended condition at which said control head is positioned distant from said operating head.

25. An instrument as set forth in claim 24 wherein said means for moving said support member enables said flexible body to move in a linear fashion in and out of said flexible guide member.

26. In an inspection instrument having a generally elongated flexible body extending between a control head at a proximal end thereof and an objective assembly at a distal end thereof for viewing subject matter to be inspected, and improvement comprising:
   a tubular elongated flexible guide member adapted to slidably receive said body therethrough including:
   an operating head at a near end of said guide member;
   a distal collar at a remote end of said guide member capable of deflection in at least two discrete directions; and
   a tubular elongated rigid support member intermediate said control head and said operating head and attached at its ends, respectively, to said control head and said operating head, said support member adapted to slidably receive said body therein;
   whereby said guide member is effective to similarly move said objective assembly when said distal end is generally coextensive with said remote end.

27. An inspection instrument as set forth in claim 26 wherein said guide member includes:
   a plurality of actuating elements movably mounted on said operating head; and
   a plurality of operating cables extending between said near and said remote end, each of said operating cables being operatively connected to said distal collar and to one of said actuating elements, respectively;
   whereby movement of each of said actuating elements is effective to deflect said distal collar in one of said directions.

28. An instrument as set forth in claim 26 wherein said support member includes:
   a plurality of coaxial telescoping sections movable between a retracted condition at which said control head is positioned proximate to said operating head and an extended condition at which said control head is positioned distant from said operating head.

29. An instrument as set forth in claim 28 wherein said objective assembly lies proximate to said distal collar when said support member assumes the extended condition and lies distant from and beyond said distal collar when said support member assumes the retracted condition.

30. In an inspection instrument having a generally elongated flexible body extending between a control head at a proximal end thereof and an objective assembly at a distal end thereof for viewing subject matter to be inspected, the improvement comprising:
   a tubular elongated flexible guide member having an interior surface and adapted to slidably receive said flexible body therethrough including:
   an operating head at a near end of said guide member;
   a distal collar at a remote end of said guide member capable of deflection in at least two discrete directions; and
   operative means for deflecting said distal collar including:
   a plurality of actuating elements movably mounted on said operating head; and
   a plurality of operating cables extending between said near end and said remote end alongside said interior surface, each of said operating cables being operatively connected to said distal collar and to one of said actuating elements, respectively, such that movement of each of said actuating elements is effective to deflect said distal collar in one of said directions; and
   said inspection instrument including:
   a tubular elongated rigid support member intermediate said control head and said operating head and attached at its ends, respectively, to said control head and said operating head, said support member adapted to slidably receive said body therein and including:
   a plurality of coaxial telescoping sections movable between a retracted condition at which said control head is positioned proximate to said operating head and an extended condition at which said control head is positioned distant from said operating head, said objective assembly lying proximate to said distal collar when said support member assumes the extended condition and lying distant from and beyond said distal collar when said support member assumes the retracted condition.

31. An instrument as set forth in claim 30 wherein said body includes an optical system for transmitting to said control head an image of the subject matter to be inspected.

* * * * *